United States Patent
Boehm et al.

(10) Patent No.: US 9,498,309 B2
(45) Date of Patent: Nov. 22, 2016

(54) MIXER FOR MIXING A DENTAL COMPOSITION

(71) Applicant: 3M Innovative Properties Company, St. Paul, MN (US)

(72) Inventors: Andreas Johannes Boehm, Reichling (DE); Marc Peuker, Schondorf (DE); Alexander Walter, Purgen (DE); Bruce R. Broyles, Oakdale, MN (US); Joel D. Oxman, Minneapolis, MN (US); John W. Dubbe, Stamberg (DE); Martin G. Hartung, Gilching (DE); Sebastian Guggenmos, Peissenberg (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/790,453

(22) Filed: Jul. 2, 2015

(65) Prior Publication Data
US 2015/0297325 A1    Oct. 22, 2015

Related U.S. Application Data

(62) Division of application No. 12/994,176, filed as application No. PCT/US2009/043881 on May 14, 2009, now abandoned.

(60) Provisional application No. 61/058,363, filed on Jun. 3, 2008.

(51) Int. Cl.
*B01F 5/06*    (2006.01)
*A61C 9/00*    (2006.01)
(Continued)

(52) U.S. Cl.
CPC .............. *A61C 9/0026* (2013.01); *A61C 5/064* (2013.01); *B01F 5/0614* (2013.01); *B01F 5/0615* (2013.01); *B01F 7/00* (2013.01); *B01F 7/00125* (2013.01); *B01F 7/00141* (2013.01); *B01F 13/002* (2013.01); *B01F 13/0023* (2013.01); *B01F 15/00831* (2013.01);
(Continued)

(58) Field of Classification Search
CPC ..................................................... B01F 5/0614
USPC ............................. 366/143, 181.5, 336–340
See application file for complete search history.

(56) References Cited

U.S. PATENT DOCUMENTS

| 1,547,562 A | 7/1925 | Byrd |
| 2,309,124 A * | 1/1943 | Knott ................. A61M 1/3681 250/437 |

(Continued)

FOREIGN PATENT DOCUMENTS

| WO | WO 02/092021 | 11/2002 |
| WO | WO 02/092023 | 11/2002 |
| WO | WO 2007/140440 | 12/2007 |

OTHER PUBLICATIONS

Johnson, James, Selection of Materials for UV Optics, Dec. 1, 2008.*

(Continued)

*Primary Examiner* — David Sorkin

(57) ABSTRACT

A mixer for mixing a dental composition comprises a mixer housing with a wall of the mixer housing forming a light filter. The light filter provides for substantially blocking light of certain wavelengths, whereas it transmits light of at least some other wavelengths. The invention may help to prevent dental compositions from degrading.

13 Claims, 4 Drawing Sheets

(51) Int. Cl.
  *B01F 7/00* (2006.01)
  *B01F 13/00* (2006.01)
  *B01F 15/00* (2006.01)
  *A61C 5/06* (2006.01)
  *B01J 19/18* (2006.01)

(52) U.S. Cl.
  CPC ......... *B01F 15/00857* (2013.01); *B01J 19/18* (2013.01); *B01F 2215/0027* (2013.01)

(56) References Cited

U.S. PATENT DOCUMENTS

| | | | |
|---|---|---|---|
| 3,610,762 A | 10/1971 | Dugan | |
| 4,538,920 A | 9/1985 | Drake | |
| 4,753,536 A | 6/1988 | Spehar et al. | |
| 5,145,886 A | 9/1992 | Oxman | |
| 5,328,462 A | 7/1994 | Sawhney et al. | |
| 5,478,150 A | 12/1995 | Keller | |
| 5,545,676 A | 8/1996 | Palazzotto et al. | |
| 6,116,900 A | 9/2000 | Ostler | |
| 6,187,836 B1 | 2/2001 | Oxman | |
| 6,394,314 B1 | 5/2002 | Sawhney | |
| 6,464,936 B1 * | 10/2002 | Mowat | A61L 2/0011 250/438 |
| 6,818,682 B2 | 11/2004 | Falsafi et al. | |
| 6,953,535 B2 | 10/2005 | Hecht | |
| 6,964,985 B2 | 11/2005 | Karim et al. | |
| 7,090,721 B2 | 8/2006 | Craig et al. | |
| 7,156,911 B2 | 1/2007 | Kangas et al. | |
| 7,649,029 B2 | 1/2010 | Kobl | |
| 8,129,444 B2 | 3/2012 | Hecht | |
| 2003/0138346 A1 * | 7/2003 | Gunn | A61L 2/0011 422/24 |
| 2003/0205454 A1 | 11/2003 | Hlavinka | |
| 2005/0014861 A1 * | 1/2005 | Qian | A61K 6/0017 523/116 |
| 2011/0189059 A1 | 8/2011 | Boehm | |

OTHER PUBLICATIONS

International Search Report for International Application No. PCT/US2009/043881, dated Aug. 31, 2009.

Nordberg, "Properties of some VYCOR-brand Glasses", Journal of the American Chemical Society, vol. 27, No. 10, pp. 299-305, (1944).

* cited by examiner

MIXER FOR MIXING A DENTAL COMPOSITION

CROSS REFERENCE TO RELATED APPLICATIONS

This application is a divisional of U.S. application Ser. No. 12/994,176, filed Mar. 9, 2011, which is a national stage filing under 35 U.S.C. 371 of PCT/US2009/043881, filed May 14, 2009, which claims priority to U.S. Provisional Application No. 61/058,363, filed Jun. 3, 2008, the disclosures of which are incorporated by reference in their entireties herein.

FIELD OF THE INVENTION

The invention relates to a mixer with an exterior wall that provides a light filter for light of certain wavelengths. The invention further relates to a delivery system furnished with such a mixer and a use of the mixer with a dental composition.

BACKGROUND ART

In dentistry hardenable dental compositions are often provided as two-component compositions stored in dual-barrel containers. The components are typically dispensed from such containers only shortly before use and mixed to form the hardenable dental composition. Dental compositions provided in that form include, for example, dental impression materials, dental filling materials, and temporary dental restoration materials.

Containers of this type are often connected or connectable with a mixer that mixes the components as they are extruded from the container. The container therefore typically has at a front end an opening for supplying the components from the individual barrels to the mixer. The container on the rear end further typically has or is prepared to receive pistons or plungers inserted in the barrels for forcing the components towards the opening and the mixer.

There are multi-dose containers that have a capacity to store enough composition for multiple uses. Such multi-dose containers typically have exchangeable mixers to allow for replacement of used mixers so that the container is usable each time with a fresh mixer. Typically the used mixer is left on the container after use, and is only replaced by a new mixer immediately prior to the next use of the container. This enables the composition in the used mixer to cover the openings of the barrels while awaiting the next use, which prevents the components in the barrels from being exposed to the environment between successive uses of the container.

For example, U.S. Pat. No. 4,538,920 discloses a dispensing device which has a syringe with an outlet, to which a static mixer is attachable.

It is generally desirable that the components of dental compositions can be stored in the container over a relatively long time without degradation or hardening. It is also desirable that containers as described without substantial modification are compatible to be used with different types of dental compositions. There is also a general need for multi-dose containers that provide a relatively long open-package shelf life for dental compositions. Other desires are to achieve reliable mixing of the components in the mixer, and to achieve a consistent quality of the mixed compositions after hardening.

It is further desired to provide dental compositions in relatively inexpensive containers, for example in containers as they are established on the market.

SUMMARY OF THE INVENTION

In a first aspect the invention is directed to a mixer for mixing a dental composition. The mixer comprises a mixer housing with a wall of the mixer housing forming a light filter. The term "light filter" is defined within this specification as providing:

a first transmittance of light within a first wavelength range, and a second transmittance of light within a second wavelength range, wherein the first transmittance is below 5% over the first wavelength range, the second transmittance is above 20% over the second wavelength range, and the first and second wavelength ranges are comprised within a spectrum of 10 nm to 1000 nm.

Preferably the second wavelength range at least partially covers the wavelength range of visible light. The wall of the mixer housing may therefore be generally transparent or translucent, but may substantially block light within a certain range of the light spectrum. The spectrum of "visible light" in this specification is defined as a spectrum of about 380 nm to 750 nm, although some sources may use different end points for that range.

There are dental compositions which are hardenable by exposing them to light. Such light hardenable compositions may be prepared by mixing together two or more individual components. The mixed composition may then be exposed to light for hardening. Typically such dental compositions comprise light activatable ingredients, so-called photo initiators, which cause a chemical reaction from which the mixture polymerizes and thus hardens. Photo initiators are typically activatable by light of a certain wavelength and intensity, which may be visible or invisible light. Photoinitiators as typically used in dentistry are only activatable by light within a wavelength range of about 400 nm to about 500 nm. The components of light hardenable dental compositions may in addition to the photo initiators further comprise ingredients that, when brought together for example by mixing the components, cause a redox reaction from which the mixture polymerizes and hardens. Such so-called "dual hardenable" compositions therefore may have two different reaction mechanisms, a light initiated reaction mechanism and a redox reaction mechanism. Typically dual hardenable materials are adapted so that the light initiated reaction proceeds at a higher rate than the redox reaction. Therefore dual hardenable compositions may remain soft for a relatively long time after mixing of the components which may facilitate the application of the compositions to a desired location. On the other hand dual hardenable compositions may be hardened quickly by exposing them to light, for example as soon as the composition is properly applied to the desired location. As an advantage portions that remain unhardened from light initiated reaction typically further hardens by the redox reaction, so that finally all of the composition hardens properly. This provides dual hardenable compositions to be used easily and at a relatively high probability of success. Dual hardening dental compositions as they may be used with the present invention are disclosed in U.S. Pat. Nos. 5,145,886, 6,187,836, 6,818,682, 6,964,985, 7,090,721, 7,156,911, US-A-2005/0256223, US-A-2007/0039519, WO 02/092021, WO 02/092023, WO 2007/140440 which are incorporated by reference herein.

The invention may be advantageous in the mixing of light hardenable compositions. For example the invention may provide for protecting the photo initiators from light prior to mixing of the components. Therefore the light initiated reaction may be generally inhibited prior to and during mixing so that the components may be prevented from altering in viscosity. This further may also provide for a relatively reliable mixing quality because variability in viscosity may also cause variability in mixing quality.

The invention may further allow a user to observe the components as they are mixed. This may be advantageous in that the user may monitor the components to estimate mixing quality. Furthermore the user may recognize the moment when the initial mixture leaves the mixer, which may help the user to position the mixer in time for dispensing the mixture to a desired location.

The invention may on the other hand be advantageous in that during storage at least the unmixed components in the mixer may be prevented from light initiated hardening. This may for example provide for the mixer to generally remain detachable from a container. For example, unmixed components having photo initiators for hardening may stay generally soft during storage due to the light filter employed in the mixer of the invention. Similarly mixers that are movably connected or connectable to a container may therefore generally remain repositionable, for adjusting the mixer, for example. As another advantage of the invention the components in the container may be less likely to change properties during storage. This may be achieved in case the mixer is used to close the outlets of the container. The mixer may keep light of wavelengths suitable to activate the photo initiators away from components that are located in the outlets, and/or at the vicinity of the outlets. Thus the invention may help to prevent blocking of the outlets during storage of the container so that the container remains useable, for example the next time a new mixer is attached to it.

In one embodiment the first transmittance is below 5% over the first wavelength range, and the second transmittance is above 20% over the second wavelength range. Preferably the first transmittance is below 2%, in more particular about 1%, about 0.5%, about 0.1% or substantially 0. The second transmittance may be above 20%, preferably above 50% and particularly above 70%, above 90% or about 95%. Therefore the term "light filter" may particularly include the first transmittance to be below 2%, about 1%, about 0.5%, about 0.1%, or substantially 0 over the first wavelength range. Further the term "light filter" may particularly include the second transmittance to be above 50%, above 70%, above 90%, or about 95%.

In another embodiment the first and second wavelength ranges are comprised within the spectrum of visible light (spectrum from about 380 nm to about 750 nm). The first and second wavelength ranges may also together cover the spectrum of visible light. Preferably the first wavelength range is a continuous range over at least 60 nm. In more particular the first wavelength range may be a continuous range over at least 30 nm or 40 nm. The term "continuous range" in the scope of this specification generally includes all values between the limits of the range.

In another embodiment the first wavelength range is a continuous range from about 400 nm to about 500 nm. A mixer having a light filter providing a low transmittance in that range may enable the unmixed components of a light hardenable dental composition to maintain their properties, for example to stay soft, while awaiting use.

In another embodiment the entire second wavelength range is outside the first wavelength range. For example the second wavelength range may range from about 600 nm to at least 800 nm. Therefore a mixer having a light filter providing a high transmittance in that range may allow a user to observe components and/or the mixture as it passes through the mixer. The user thereby may be able to monitor the mixing uniformity and quality, for example.

In a further embodiment of the invention the mixer comprises a mixing element. The mixing element is preferably disposed in the housing, and in particular may be surrounded by the housing. The mixer housing may comprise in at least an area surrounding the mixing element the wall forming the light filter. The wall may be made of a material that provides the light filter of the invention. The mixer housing may also be substantially entirely formed by a material providing the light filter of the invention. An embodiment of a one-piece mixer housing made of the same material may provide for relatively inexpensive manufacturing, for example.

In one embodiment the mixer further comprises an inlet and an outlet. Preferably at least part of the mixer housing forms a mixing barrel which surrounds the mixing element. Furthermore the mixing barrel is preferably adapted for guiding components of the dental composition from the inlet toward the outlet for mixing. For example, the mixing barrel may resemble an elongated tube arranged between the inlet and the outlet of the mixer. The mixing element may be arranged in the mixing barrel so that components forced through the barrel pass by or pass through the mixing element and are thereby mixed.

In one embodiment the mixing element comprises a series of guiding blades that are fixedly arranged relative to the mixing barrel. Such fixedly arranged guiding blades together with the mixing barrel typically form a static mixer. The guiding blades of such static mixer are typically helically shaped and disposed spaced from each other along the mixing barrel to divide and merge the composition multiple times as it passes the mixer. Another type of mixing element used to form a static mixer is the Quadro® Mixer as available from the company Sulzer Chemtech Ltd., Switzerland.

In another embodiment the mixing element is however a mixing rotor of a dynamic mixer. A mixing rotor is typically rotatably arranged in the mixer housing so that it can be driven by a drift shaft, for example, and comprises mixer paddles that, when the mixing rotor turns, transversely shear the composition encountered by the mixer.

The mixing element of the mixer may have a certain color which represents a certain property or suitability of the mixer. For example, the color of the mixing element may indicate the suitability to mix a certain dental substance, while another color may indicate the suitability to mix an industrial adhesive, for example. Thereby a user may select an appropriate mixer for a desired application. In dentistry this may in particular help to ensure that mixers used for treating patients fulfill certain hygiene requirements.

In another embodiment the mixing element has a color which is different from the color of the substance mixed. For example, the dental substance may be generally tooth colored, and the mixer may have a distinct color (like red, green or blue, for example). This may provide the user to better assess the mixing quality of the substance as it flows through the mixer.

A second aspect of the invention concerns a delivery system for a dental composition. The delivery system comprises:

a mixer according to the invention;

a cartridge having a first and second compartment for receiving a first and second component of the dental composition; and a piston in each of the compartments for advancing the components towards the mixer.

In another embodiment the mixer is movably connected or connectable to the cartridge. The mixer with the cartridge thereby preferably forms a valve for connecting and disconnecting the mixer with the first and second compartments. For example, the mixer may in a first position relative to the cartridge close off the first and second compartments, and in a second position be in fluid communication with the first and second compartments. The mixer therefore may during storage, for example when it closes off the first and second compartments, prevent components stored in the cartridge prevent from getting exposed to light of certain wavelengths. Thus the cartridge may provide a relatively long shelf life, but still provide the advantages resulting from a generally transparent or translucent wall of the mixer housing.

In a further embodiment the delivery system is connectable to an applicator device. The applicator device may have a plunger which is adapted to advance the pistons in the compartments of the delivery system. The applicator device may also have multiple plungers which are adapted to, preferably synchronously, advance each of the pistons in the compartments of the delivery system. The applicator device may have an actuator that can be manually operated to advance components stored in the compartments of the delivery system towards the mixer, and to advance the mixture out of the mixer to a desired place. Exemplary applicators as they may be usable with the present invention are available under the designation "Aplicap Applier", "Garant Dispenser", or "Capsule Dispenser" from the company 3M ESPE AG, Germany. In another embodiment of the invention the delivery system comprises an applicator, wherein the applicator has a lever which, when actuated, causes a plunger to advance. Such delivery system is preferably adapted to be held by a user like a pen, with the lever being arranged so that it can be actuated with a finger. The delivery system may thus provide for a handling that is particularly advantageous for positional precise dispensation of the dental substance.

A third aspect of the invention relates to a combination or a system of a mixer according to the invention for providing a dental composition. The third aspect of the invention further relates to a combination or a system of a delivery system of the invention.

In one embodiment a system comprises a mixer according to the invention and a light hardenable dental composition.

In another embodiment a system comprises a delivery system of the invention and a light hardenable dental composition.

The light hardenable composition may, independent from ingredients causing a light initiated reaction, further comprise ingredients that are adapted or selected to cause a redox reaction, for example without the presence of light.

In one embodiment the dental composition is selected from among filling materials, temporary crown and bridge materials, varnishes, sealants, bondings, adhesives, impression materials, and luting materials. A suitable dental filling material may be for example a resign modified glass-ionomer material.

Compositions as they may be used with the present invention are disclosed in incorporated references U.S. Pat. Nos. 5,145,886, 6,187,836, 6,818,682, 6,964,985, 7,090,721, 7,156,911, US-A-2005/0256223, US-A-2007/0039519, WO 02/092021, WO 02/092023, WO 2007/140440.

Preferably at least one component of the dental composition has a photo initiator.

Suitable photoinitiators for hardening dental compositions may include an iodonium salt, a photosensitizer, and an electron donor compound as described in U.S. Pat. No. 5,545,676 (Palazzotto et al.). Preferred iodonium salts are the diaryl iodonium salts, for example, diphenyliodonium chloride, diphenyliodonium hexafluorophosphate, diphenyliodonium tetrafluoroborate, and tolylcumyliodonium tetrakis(penta-fluorophenyl)borate. Preferred photosensitizers are monoketones and diketones that absorb some light within a range of about 400 nm to 520 nm preferably, 450 nm to 500 nm. More preferred photosensitizers are alpha diketones that have some light absorption within a range of 400 um to 520 nm (even more preferably, 450 to 500 nm). Other preferred photosensitizers are camphorquinone, benzil, furil, 3,3,6,6-tetrarmethylcyclohexanedione, phenanthraquinone, 1-phenyl-1,2-pro-panedione and other 1-aryl-2-alkyl-1,2-ethanediones, and cyclic alpha diketones. Preferred electron donor compounds include substituted amines, for example, ethyl dimethylaminobenzoate.

A fourth aspect of the invention relates to a kit of parts, comprising a plurality of mixers according to the invention, and at least one dental composition. The kit may for example comprise a multi-dose cartridge filled with components suitable to form a dental hardenable composition, and a plurality of mixers according to the invention. Further, the kit may comprise a plurality of mixers according to the invention and a plurality of cartridges. In one embodiment each of the plurality of mixers may be connected with one of the plurality of cartridges. In this embodiment the mixers are preferably static mixers that are movably connected to the cartridges. Each of the static mixers with the respective cartridge preferably forms a valve for connecting and disconnecting the static mixer with compartments of the cartridge that store the component of the dental composition.

DETAILED DESCRIPTION OF THE INVENTION

A light filter according to the invention may be generally transparent or translucent, but may substantially block light of certain wavelengths. A mixer having a wall that forms a light filter according to the invention may in particular be used with compositions that are mixed from components which have a light sensitive ingredient, for example an ingredient which is light-activatable to cause hardening of the composition. Because of the transparency or translucency of the mixer wall a user may be able to observe composition dispensed through the mixer. On the other hand the mixer wall may protect the individual components and the mixture from being exposed to light wavelengths that are capable of causing the components and/or the mixed composition to alter in properties, for example to harden.

In particular such a mixer may be used with light hardenable dental compositions which have light activable ingredients. Such a mixer may further be used with light hardenable dental compositions comprising chemically reacting ingredients. Dental compositions may be generally provided in delivery systems, as for example illustrated in FIG. 1 or 4, that allow storage of two or more components separate from each other. In the following embodiments of the invention is explained in more detail by way of example.

Figure 1:
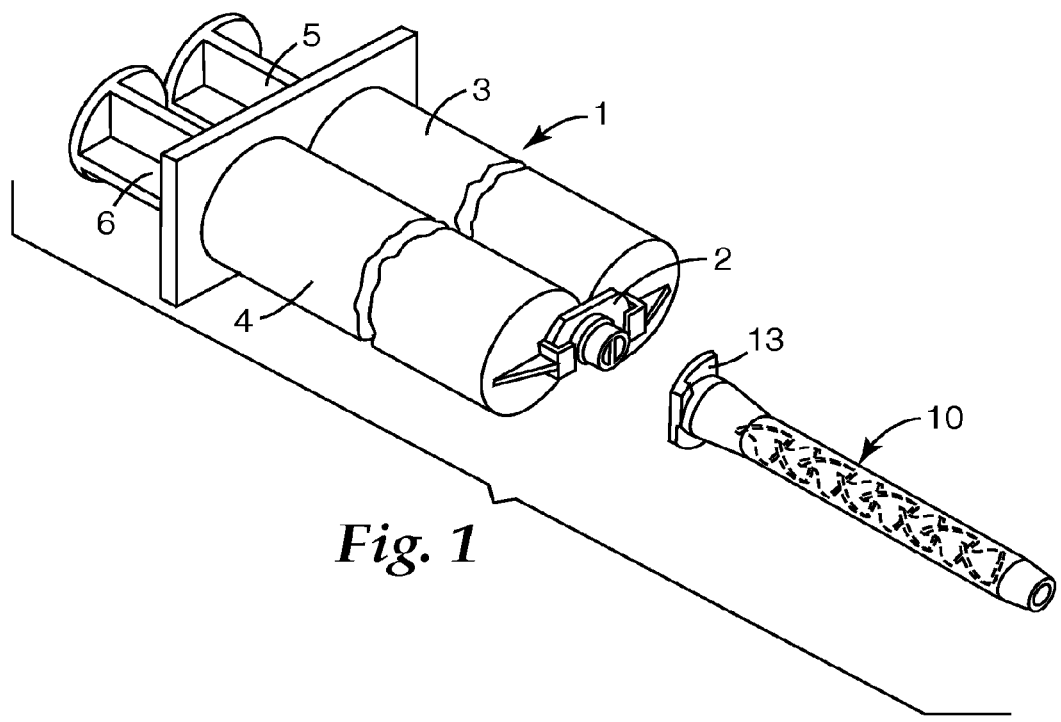
FIG. 1 is a perspective view of a container according to the prior art, and a static mixer according to the invention.

FIG. 1 shows a static mixer 10 according to the invention and an exemplary container 1 usable with the static mixer 10. The static mixer 10 shown has a coupling end 13 which allows the static mixer 10 to be attached to adapter 2 of the container 1. Therefore the static mixer 10 is detachably mountable to the container so that a used mixer may be replaced by a new or unused one for further use of the container 1. This is particularly advantageous for example for application of hardenable components because a mixer blocked by hardened components may be easily replaced by a new mixer so that the container remains usable. Thus, the container may be used for dispensing multi-component hardenable compositions in several smaller portions with storage periods in between as desired. The container 1 has plungers 5, 6 which can be moved into the container 1 to supply components stored in the barrels 3, 4 into the static mixer 10 for mixing and subsequent application to a desired location.

Figure 2:
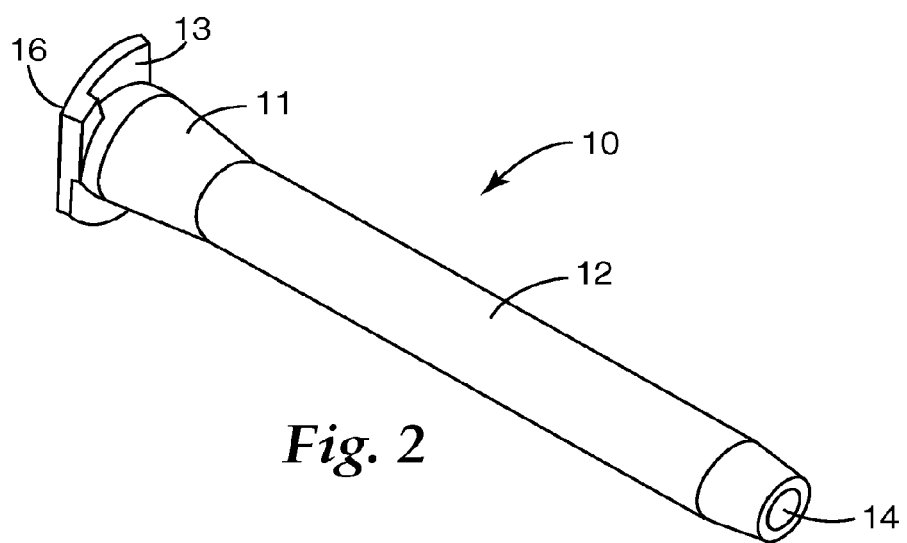
FIG. 2 is a perspective view of a static mixer according to an embodiment of the invention.
Figure 3:
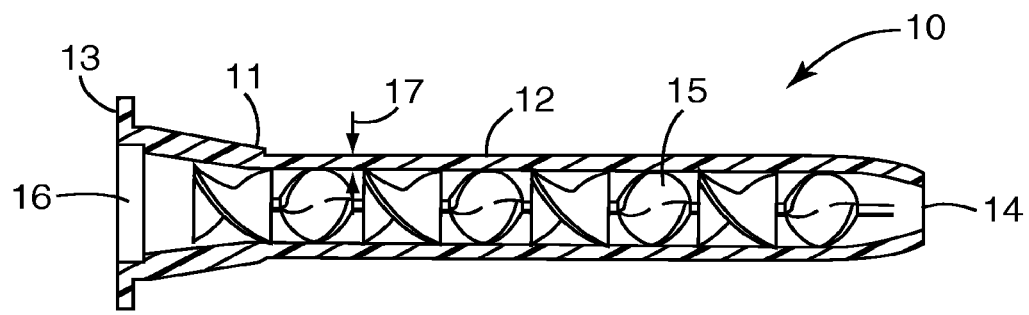
FIG. 3 is a cross-sectional view of the static mixer shown in FIG. 1 and FIG. 2.

FIGS. 2 and 3 show the static mixer 10 in more detail. The configuration of the static mixer 10 is described with reference to the cross-sectional view shown in FIG. 3. However FIG. 2 depicts certain features from an exterior perspective view for better clarity. The static mixer 10 has a mixer housing 11 with an elongated mixing barrel 12, and coupling end 13. The static mixer 10 comprises a mixing element 15, which in the example is a so-called mixing helix. The mixing helix typically comprises a plurality of helically shaped mixing blades that are arranged along and project relative to a central axis. Components passing by or through the mixing helix are typically divided and merged multiple times to achieve preferably complete intermingling or mixing of the components to form a mixture. However, there are other mixing elements that may be used with the present invention, for example mixing elements as used in the Quadro® Static Mixers, as available from Sulzer Chemtech AG, CH-8404 Winterthur, Switzerland. The barrel 12 of the mixer housing 11 surrounds the mixing element 15 and forms a channel for guiding components supplied into the inlet 16 of the mixer 10 towards the outlet 14. There is preferably relatively little or no clearance between the mixing element and the interior walls of the barrel 12 so that the components are forced to pass through the mixing element 15. A wall 17 of the mixer housing 11 forms a light filter as specified as a feature in certain embodiments of the invention. For example, the wall may be generally transparent or translucent, but may block visible or invisible light of a certain color. In the example shown, preferably the entire barrel 12 forms a light filter. More preferably the mixer housing 11 may be made of a material that filters light. For example the mixer housing 11 may be molded from a generally transparent or translucent plastic material which is compounded with additives providing for blocking light of a certain color. For example an additive blocking light within a range of the sensitivity of a photo initiator therefore may prevent light-activatable components from hardening.

Plastic materials usable for the mixer housing may be acrylonitrile methacrylate, polypropylene, polyethylene, polybutadiene terephthalate, polycarbonate, polymethyl methacrylate, for example.

Additives that may be used with at least certain of the mentioned plastic materials are for example:

Polysythren Yellow GG, Chem. group: Methine, CAS No. 51202-86-9

Polysyntren Red 2G, Chem. group: Perinone, CAS No.: 89106-94-5

Solvaperm Orange 3G, Chem. group: Perinone, CAS No.: 6925-69-5, and

Solvaperm Red 2G, Chem. group: Azomethine Ni-Complex, CAS No.: 61300-98-9 all available from Clariant International AG, Switzerland.

Figure 4:
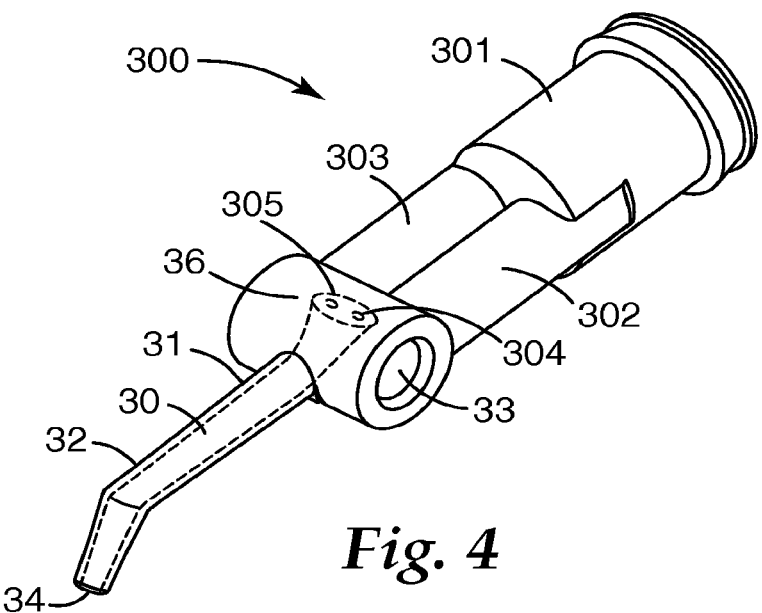
FIG. 4 is a perspective view of a delivery system for a dental composition according to an embodiment of the invention.

FIG. 4 shows a capsule 300 having a cartridge 301 with two compartments 302, 303 for storing two components of a composition, for example a light hardenable dental composition. The capsule 300 further has a static mixer 30 (not explicitly shown) with a mixer housing 31 and a mixing element (not shown) disposed therein. The mixer housing 31 has a generally cylindrical coupling element 33 which is rotatably attached to the cartridge 301. The coupling element 33 comprises an inlet 36 (indicated as hidden structure) which in the position of the static mixer 30 shown in FIG. 4 is connected to outlets 304, 305 of the compartments. Both compartments are therefore open to provide a supply of the components in the mixer 30, which after mixing may be dispensed from the outlet 34 of the mixer 30. The static mixer 30 when positioned in a storage position, for example in the figure positioned substantially 90 degrees towards the bottom of the page from the position shown, closes off the outlets. In this example, at least the wall of the mixer housing 31 which closes off the outlets preferably forms a light filter within the meaning of that feature of the invention. Therefore at least the coupling end 33 may have a wall forming a light filter. This may provide for protecting components stored in the compartments from exposure to light in the portion of the spectrum in which the components are sensitive. The components may thereby be stored over a relatively long time, and a shelf-life of the capsule of one or more years may be achieved, for example. Further, barrel 32 of the mixer 30 may have a wall forming a light filter in the sense of a feature of the invention. Preferably the mixer housing 31 is made of a material providing such light filtering effects.

Figure 5:
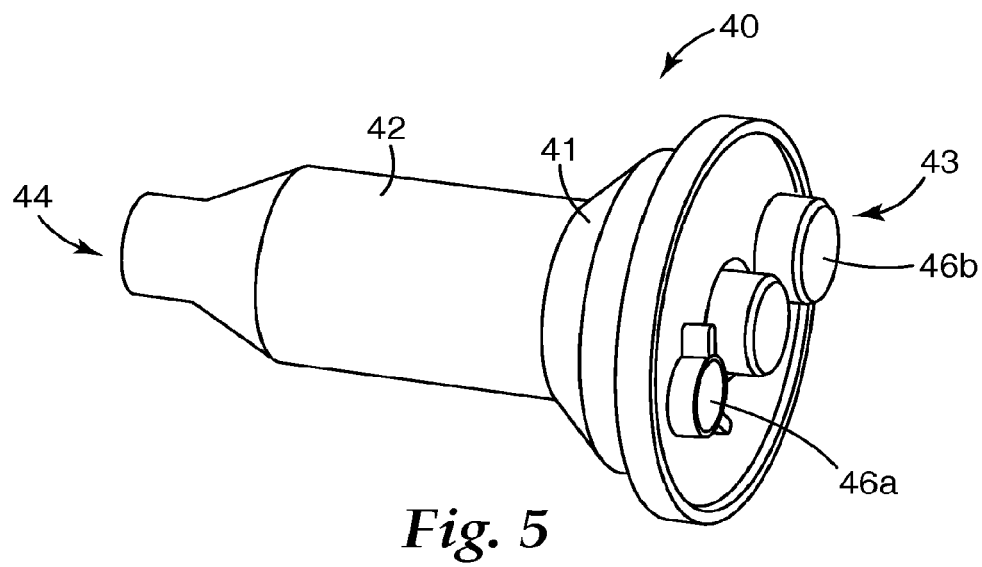
FIG. 5 is a perspective view of a dynamic mixer according to an embodiment of the invention.
Figure 6:
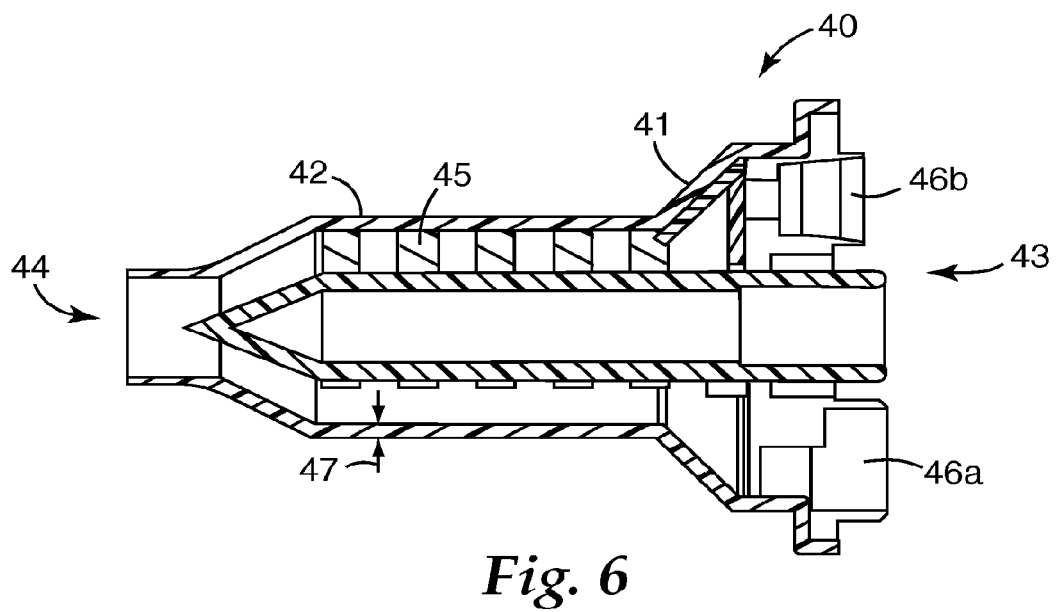
FIG. 6 is a cross-sectional view of the dynamic mixer of FIG. 5.

FIGS. 5 and 6 show a dynamic mixer 40 according to the invention, which has a housing 41. The housing 41 has an elongated mixing barrel 42. The dynamic mixer 40 is attachable to a container from which components of a composition may be supplied into the dynamic mixer 40. The dynamic mixer 40 for attachment to the container has a coupling end 43. As described with respect to an embodiment of a static mixer above this allows for example for exchange of a used dynamic mixer by a new or unused one.

FIG. 6 shows a cross-section of the dynamic mixer of FIG. 5. The dynamic mixer 40 comprises a mixing element 45, which in this example is a mixing rotor. The mixing rotor shown in the example comprises a plurality of circumferentially arranged mixing paddles. Other embodiments of mixing rotors are however possible, like for example a rotatable mixing helix. The barrel 42 of the mixer housing 41 surrounds the mixing element 45 and forms a channel for guiding components of a composition supplied into the inlets 46a, 46b of the mixer 40 towards the outlet 44 (reference numbers 46a, 46b and 44 are also depicted in FIG. 5). The barrel 42 is shaped to closely surround the mixing element 45, but generally provides a loose fit to provide rotatablity of the mixing element 45 relative to the mixing barrel 42. According to the invention a wall 47 of the mixer housing 41 forms a light filter.

Figure 7:
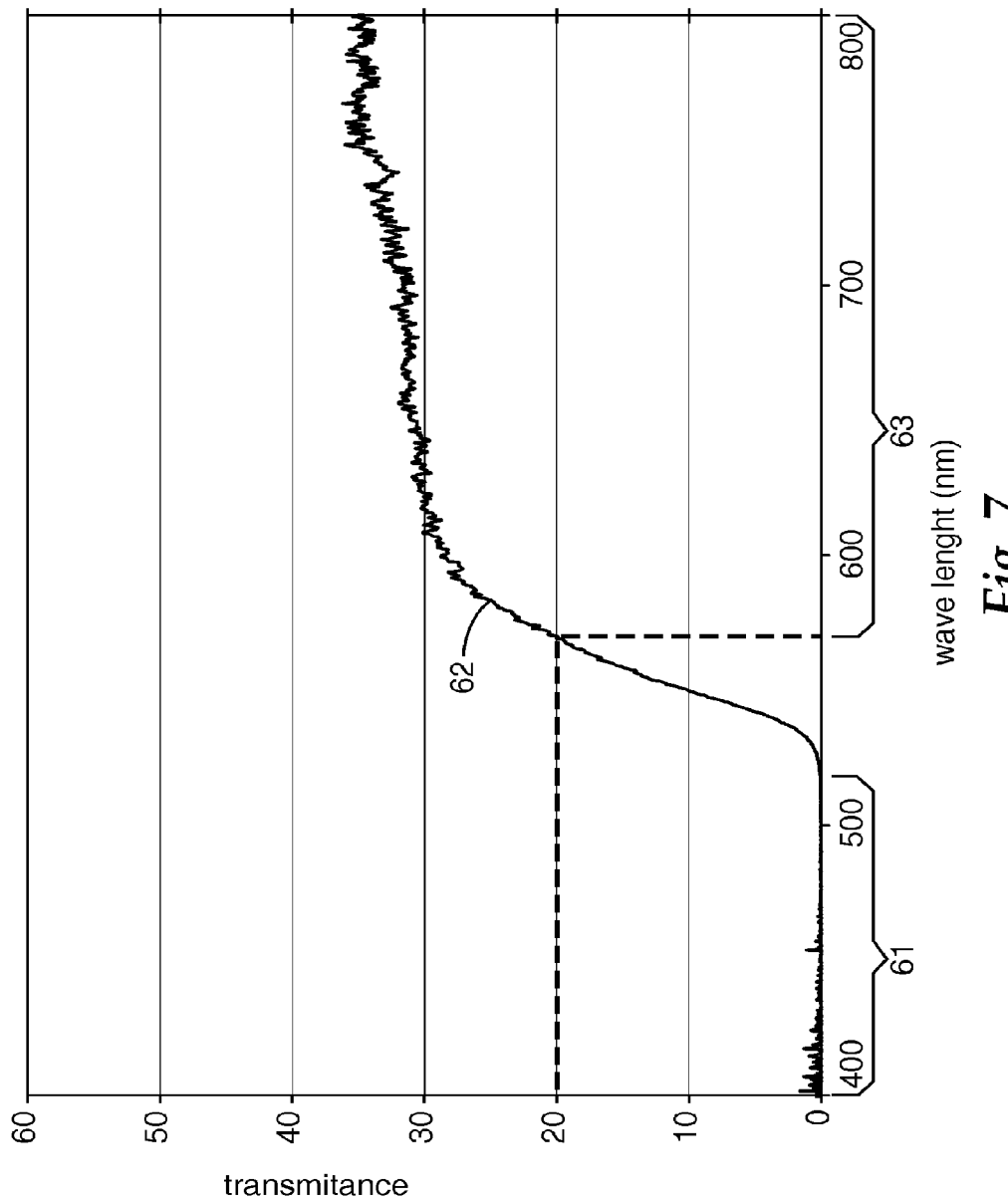
FIG. 7 is a diagram showing a light filtering characteristic according to an embodiment of the invention.

FIG. 7 shows an exemplary light filtering characteristic as it may be provided by a wall of the mixer housing according to certain embodiments of the invention. Such characteristic, for example may substantially be provided by a wall which is characterized as follows:

| | |
|---|---|
| Thickness of the wall of the mixer housing: | about 1.5 mm |
| Plastic material the wall is comprised of: | Acrylonitrile Methacrylate Copolymer as available under the designation Barex 210, nature, from the company Velox GmbH, Hamburg |
| Color-Masterbatch compounded with the plastic material | as available under the designation PAN 22972, from the company Velox GmbH, Hamburg |
| Percentage of Color-Masterbatch compounded with the Plastic material | about 2.5% by weight of plastic material |

A Color-Masterbatch is typically a compound comprising a plastic material and one or more additives, for example a plastic material and an additive as specified within this specification.

The diagram has a vertical axis representing the transmittance of the wall in % of incident light, and a horizontal axis representing wavelengths of the incident light in nanometers. The curve 62 has a section 61 representing a relatively low transmittance of the wall in a first wavelength range, and a section 63 representing a relatively high transmittance of the wall in a second wavelength range. The section 61 of relatively low transmittance is preferably below about 5% (in the example substantially 0), whereas the section 63 of higher transmittance is preferably above about 20% (in the example between about 20% and about 35%, particularly between about 30% and about 35%). Preferably the section 61 of relatively low transmittance is below a lower threshold above which a composition starts to be affected. Further, preferably the section 63 of higher transmittance provides a transparency or translucency which provides visibility of the composition through the wall. Preferably the section 63 is a continuous range within the spectrum of visible light. Further, also the range 61 may be a continuous range within the spectrum of visible light. However, instead of a continuous range the curve may have points of low transmittance at predetermined discrete wavelengths. Therefore the wall may be generally opaque for light of a certain color, but may be generally transparent or translucent for light of other colors. The example represents a wall that generally blocks light within a range of about 400 nm to 500 nm, whereas it preferably transmits light in at least some other wavelengths below and above that range. The transmittance of the wall typically also depends on the wall thickness. For example a thinner wall may result in a curve that is shifted vertically (in the Figure more toward the top), but shaped generally similarly. For example a thinner wall may in section 61 still provide for a transmittance of below about 5%, but in section 63 a transmittance of more than 30%. In contrast a thicker wall may in section 61 provide for a transmittance of far less than about 5%, whereas the transmittance in section 63 may be about 20%. Such curve would, for example, resemble the curve shown in FIG. 7, but shifted vertically (in the Figure more to the bottom). A wall as characterized by the curve 62 may for example be used with the embodiments of a mixer of the invention. Such wall may provide for blocking light of certain wavelengths to prevent compositions processed with the mixer from premature hardening, for example.

The invention claimed is:

1. A mixer for mixing a dental composition, comprising:
    a mixer housing with a wall of the mixer housing forming a light filter which provides a first transmittance of light within a first wavelength range, and a second transmittance of light within a second wavelength range, wherein the first transmittance is below 5% over the first wavelength range, the second transmittance is above 20% over the second wavelength range, with the second wavelength range at least partially covering the wavelength range of visible light, and wherein the first and second wavelength ranges are each within the spectrum of visible light ranging from about 380 nm to about 750 nm; and
    a mixing element disposed in an inner cavity of the mixer housing.

2. The mixer of claim 1, wherein the first wavelength range continuously ranges from about 400 nm to about 500 nm, and the second wavelength range is beyond the first wavelength range.

3. The mixer of claim 1, wherein the mixer housing comprises the wall forming the light filter in at least an area surrounding the mixing element.

4. The mixer of claim 1, wherein the mixer housing is substantially entirely formed by a material that provides the light filter.

5. The mixer of claim 1, wherein the wall of the mixer housing comprises a plastic material.

6. The mixer of claim 1, comprising an inlet and an outlet, wherein at least part of the housing forms a mixing barrel surrounding the mixing element, and wherein the mixing barrel is adapted for guiding components of the dental composition from the inlet toward the outlet.

7. The mixer of claim 1, wherein the mixing element is selected from among a mixing helix of a static mixer, and a mixing rotor of a dynamic mixer.

8. A delivery system for a dental composition, comprising:
    a mixer as specified in claim 1;
    a cartridge having a first and second compartment for receiving a first and second component of the dental composition; and
    a piston in each of the compartments for advancing the components towards the mixer.

9. The delivery system of claim 8, wherein the mixer is movably connected or connectable to the cartridge to form a valve for connecting and disconnecting the static mixer with the first and second compartments.

10. A system comprising the mixer of claim 1, in combination with a light hardenable dental composition.

11. The system of claim 10, wherein the light hardenable dental composition is located within the inner cavity of the mixer housing.

12. The system of claim 10, wherein the dental composition comprises camphorquinone.

13. A kit of parts, comprising;
a mixer of claim 1, and at least one dental composition located within the inner cavity of the mixer housing.

* * * * *

UNITED STATES PATENT AND TRADEMARK OFFICE
CERTIFICATE OF CORRECTION

PATENT NO. : 9,498,309 B2  
APPLICATION NO. : 14/790453  
DATED : November 22, 2016  
INVENTOR(S) : Boehm et al.

Page 1 of 1

It is certified that error appears in the above-identified patent and that said Letters Patent is hereby corrected as shown below:

On the Title Page

Column 1 item (72), (Inventors)
Line 6, delete "Stamberg" and insert -- Starnberg --, therefor.

In the Specification

Column 6
Line 22, delete "6-tetrarmethylcyclohexanedione," and insert -- 6-tetramethylcyclohexanedione, --, therefor.

Column 7
Line 16, delete "FIG." and insert -- FIGS. --, therefor.

Column 8
Line 14, delete "Polysythren" and insert -- Polysynthren --, therefor.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*